United States Patent
Scalisi et al.

(10) Patent No.: US 6,363,274 B1
(45) Date of Patent: Mar. 26, 2002

(54) APPARATUS FOR RECORDING AN ELECTROCARDIOGRAM

(75) Inventors: Gérard Scalisi, Paris; Alain Danteny, Sausset-les-Pins; Alain Piloy, Marseille, all of (FR)

(73) Assignee: Sanimat Diffusion S.A. (FR)

( * ) Notice: Subject to any disclaimer, the term of this patent is extended or adjusted under 35 U.S.C. 154(b) by 0 days.

(21) Appl. No.: 09/625,455

(22) Filed: Jul. 26, 2000

Related U.S. Application Data (63) Continuation of application No. PCT/FR99/00157, filed on Jan. 27, 1999.

(51) Int. Cl.[7] .............................................. A61B 5/0404
(52) U.S. Cl. ..................................... 600/523; 600/509
(58) Field of Search ................................. 600/508, 509, 600/513, 515, 520, 523

(56) References Cited

U.S. PATENT DOCUMENTS

| | | | | |
|---|---|---|---|---|
| 4,596,256 A | * | 6/1986 | Ascher et al. | 600/523 |
| 5,029,590 A | * | 7/1991 | Allain et al. | 600/523 |
| 5,172,698 A | | 12/1992 | Stanko | |
| 5,339,823 A | * | 8/1994 | Reinhold | 600/523 |
| 6,073,046 A | * | 6/2000 | Patel et al. | 600/374 |

FOREIGN PATENT DOCUMENTS

| | | |
|---|---|---|
| DE | 8911113.3 | 2/1989 |
| EP | 106756 | 4/1984 |
| EP | 761164 | 3/1997 |
| FR | 2666977 | 3/1992 |
| WO | WO 8805282 | 7/1988 |
| WO | WO 9403106 | 2/1994 |

* cited by examiner

*Primary Examiner*—George R. Evanisko
(74) *Attorney, Agent, or Firm*—Schnader Harrison Segal & Lewis LLP

(57) ABSTRACT

Apparatus for recording an electrocardiogram including: a portable housing; and an analyzer which acquires, processes and stores electrical signals delivered by electrodes positioned on the housing such that the electrodes may be applied to a patient's thorax, and wherein the housing has a first series of three metallic electrodes positioned for application on the patient's thorax to acquire three precordial signals, a second series of two metallic electrodes positioned on the housing so that the patient's fingers may be applied thereon, to acquire two peripheral signals, and a skin electrode to acquire a third peripheral signal, connected to the housing by a connecting cable.

16 Claims, 5 Drawing Sheets

APPARATUS FOR RECORDING AN ELECTROCARDIOGRAM

RELATED APPLICATION

This is a continuation of International Application No. PCT/FR99/00157 with an international filing dated of Jan. 27, 1999, which is based on French Patent Application No. 98/00919 filed Jan. 28, 1998.

FIELD OF THE INVENTION

The present invention relates to the field of electrocardiography. More particularly, the invention concerns a portable apparatus or device for recording an electrocardiogram.

BACKGROUND

The general principle of such devices is, in particular, known from French patent FR2645005. FR'005 describes a device for successively recording a control electrocardiogram and a second electrocardiogram from a patient, then comparing the electrocardiograms after having transmitted them to a remote computer. The device described in FR'005 requires installation of a plurality of electrodes connected to the housing via cords. The electrodes must be fixed on the body by bracelets or similar means. The relevance of such a device is mainly related to alleged seizure situations. This enables a patient to record by himself, an emergency electrocardiogram, without the presence or aid of medical personnel.

However, it is important that handling the device be simplified to the utmost. Indeed, when the patient recognizes signs of a seizure, or believes that he has recognized such signs, it is desirable that the handling operation be very simple to perform. The device from the prior art is not entirely satisfactory in this respect. Actually, this requires positioning of three electrodes on three distinct parts of the patient's body, possibly plugging the connection sockets of the cords connecting the electrodes to the portable housing and handling the device to which several cables of about a length of one meter are connected.

The publication WO94/03106 is also known from the state of the art. WO'106 is believed to comprise the closest state of the art. It discloses an acquisition housing including nine electrodes. Six of these electrodes are positioned on a housing, following a rigid curved surface. The other electrodes corresponding to peripheral signals are meant to be applied against the patient's skin, at both arms and the groin.

Satisfactory results cannot be obtained by using such a device. It is extremely difficult for a patient using this equipment by himself, to properly apply the housing on his thorax, so as to ensure excellent contact and without any "trembling" for each of the six pre-cordial electrodes. In addition to this difficulty, it should be noted that the patient must simultaneously block the two upper peripheral electrodes under his armpits.

Finally, the patient has to handle the device to trigger the recording and hold a telephone set in one hand for transmitting the vocal signal generated by the device. Unless the patient is a proven contortionist, proper use of such an equipment is virtually impossible for a patient who may be in a situation of anxiety and stress.

The invention solves this problem in a way which is not described in the prior art, and which is not obviously inferred from it.

SUMMARY OF THE INVENTION

Apparatus for recording an electrocardiogram comprising: a portable housing; and an analyzer which acquires, processes and stores electrical signals delivered by electrodes positioned on the housing such that the electrodes may be applied to a patient's thorax, and wherein the housing has a first series of three metallic electrodes positioned for application on the patient's thorax to acquire three precordial signals, a second series of two metallic electrodes positioned on the housing so that the patient's fingers may be applied thereon, to acquire two peripheral signals, and a skin electrode to acquire a third peripheral signal, connected to the housing by a connecting cable.

A system for interpreting electrocardiograms from a patient recorded by a portable device comprising: a device for recording an electrocardiogram including a portable housing and an analyzer which acquires, processes and stores electrical signals delivered by electrodes, wherein the housing has a first series of three metal electrodes positioned so that they may be applied on the patient's thorax to acquire three precordial signals and a second series of two metal electrodes positioned so that the patient's thumbs may be applied for acquiring two peripheral signals, as well as a skin electrode for acquiring a third peripheral signal, connected to the housing by a connecting cable; and, a microcomputer capable of receiving, storing and displaying information transmitted by the portable device.

BRIEF DESCRIPTION OF THE DRAWINGS

The invention will be better understood upon reading the description of a non-limiting exemplary embodiment, with reference to the appended drawings wherein.

DETAILED DESCRIPTION OF THE INVENTION

The following description is intended to refer to specific embodiments of the invention illustrated in the drawings and is not intended to define or limit the invention, other than in the appended claims. Also, the drawings are not to scale and various dimensions and proportions are contemplated.

Figure 1:
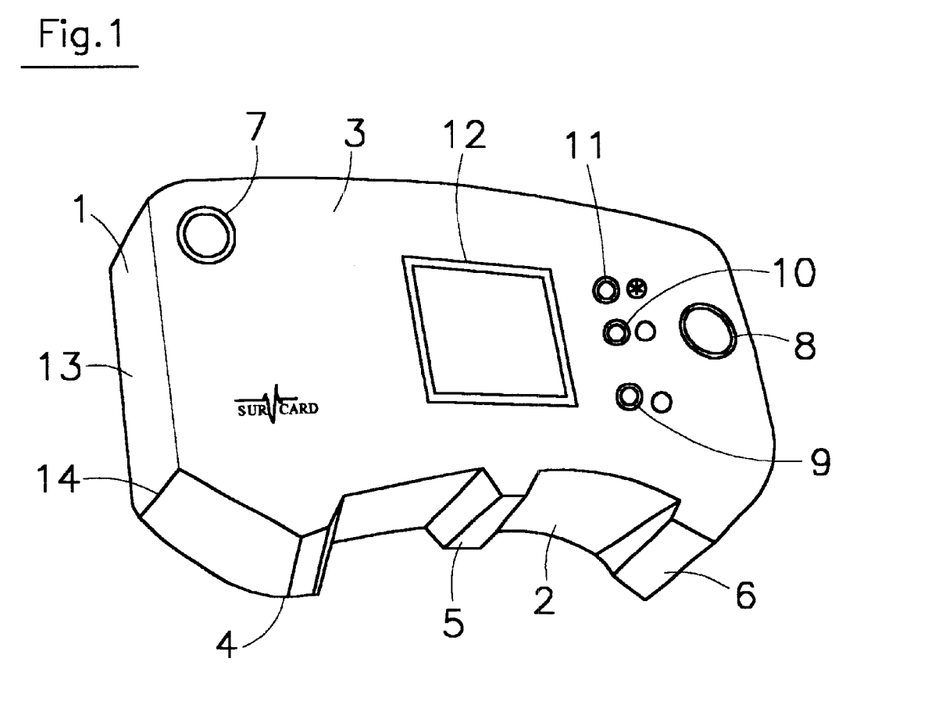
FIG. 1 shows a perspective view of the housing according to the invention.

The device according to the exemplary embodiment described as non-limiting, comprises a plastic housing having a thickness of about 60 mm and a width of about 200 mm. It has a concave front face 2 and an upper face 3 provided with monitoring means.

The concave front face 2 has three metal electrodes 4, 5, 6 transversely positioned with respect to the concave face. The electrodes have a contact surface which is about 10 mm wide and about 35 mm high. The radius of curvature of the concave front face 2 is about 300 mm and the distance between two consecutive electrodes is about 60 mm.

The upper face 3 has two metal electrodes 7, 8 of circular shape, having a diameter of about 15 mm. Furthermore, the upper face 3 has control buttons 9, 10, 11 for starting and stopping the device, and for selections with the aid of a menu appearing on a display screen 12. This screen 12 allows textual information to be displayed as well as graphical information.

The housing further comprises a cord terminating with a skin electrode of the "keel" type. This electrode has the shape of a metal conductor with a length of about 40 mm and with a cross section of about 5 mm, preferably made of chromium plated brass. An electrical conductor is soldered on one of its ends. A plastic cap is molded from a casting on the solder. This molded cap protects the electrical connection. The side face 13 of the housing has a trapdoor 14 which may be shut by a movable or hinged flap. This trapdoor protects a connector which plugs into a multistandard connector, for connecting the portable recorder to a classical electrocardiograph. To prevent improper plugging of cords, especially cords connected to the mains, opening the flap actuates a switch which controls insulation of the electrodes 4–8 and of the skin electrode.

Figure 2:
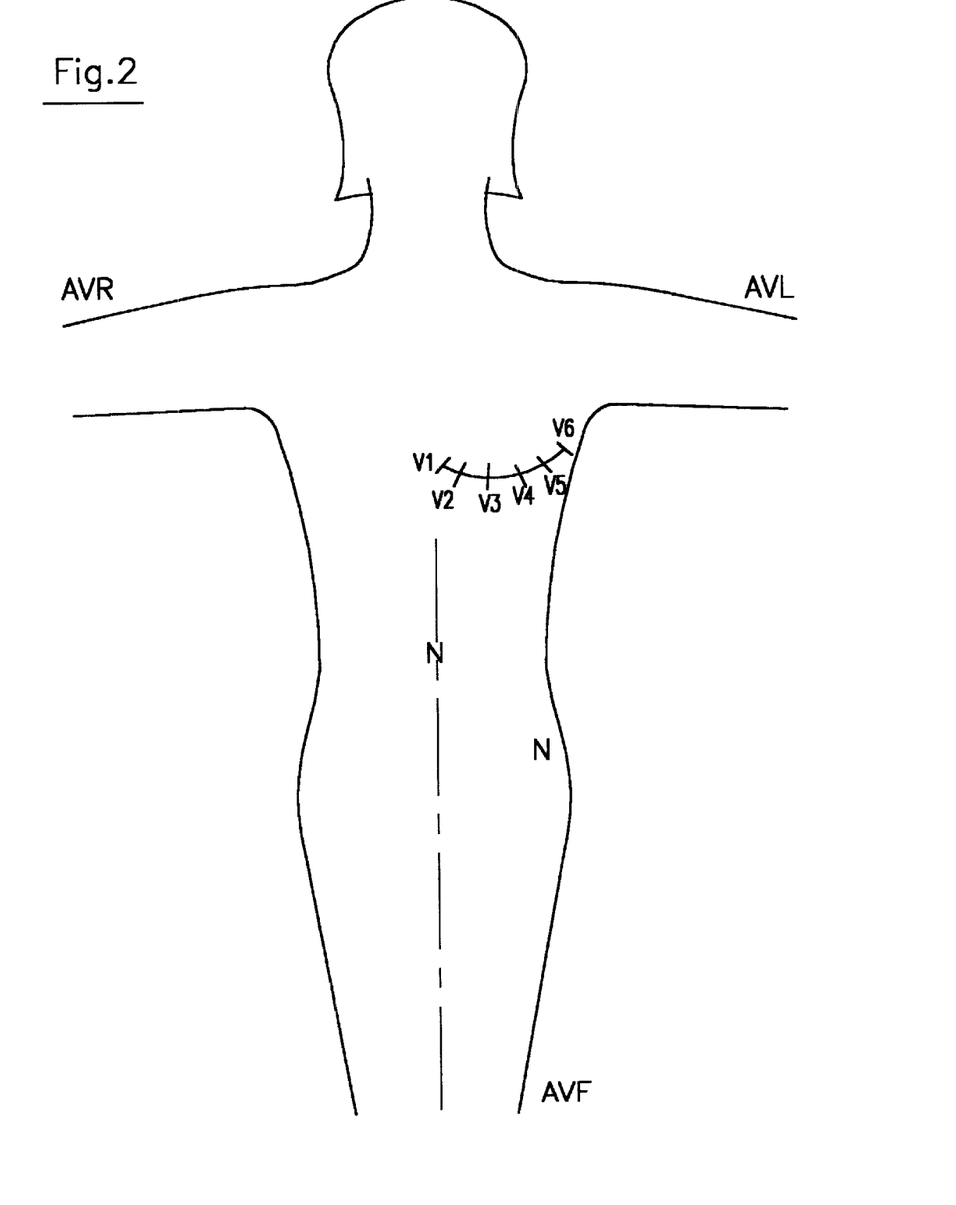
FIG. 2 shows a schematic view of the positioning of the device during its use.

FIG. 2 shows a schematic view of the use of the housing. The patient applies the housing against the thorax, by holding it with both hands. The right thumb is applied on the electrode 8 and the left thumb on the electrode 7. The central electrode 5 is applied under the patient's nipple, and the two side electrodes 4, 6 are applied against the patient's chest, on both sides of a substantially horizontal line.

The center electrode 5 is thus applied against the V3 precordial point, and the side electrodes 4, 6 against the V2 precordial point, and against a point located between the precordial points V4 and V5. The signal corresponding to the V3 precordial point is processed to provide a signal corresponding to neutral.

The device provides simultaneous recording of five leads and reconstruction of three additional leads for storing and displaying eight leads of the electrocardiogram D1, D2, D3, aVR, aVL, aVF, V2 and V5 for a period of a few seconds, for example 12 seconds. Through an external patient cord, a complete recording of 12 leads may be performed by the physician.

The signals acquired through the six electrodes are processed in a globally known way. First, they are pre-amplified, then digitized by an analog/digital converter. These digital signals are then filtered to suppress noise such as "50 Hz" signals and various predictable artifacts.

The thereby processed signal is then stored in a non volatile memory including six locations in the described example. Recording a new series of signals causes the oldest recording to be deleted. These data may also be displayed on the screen 12 graphically.

In a first exemplary embodiment, the device provides simultaneous recording of five leads for 12 seconds, calculation of three additional leads and storage of eight or more plots, comparison with one or two reference electrocardiograms and remote transmission of the stored data.

The digitized and pre-processed signals are also interpreted by an "expert system" software package, which performs the extraction of a plurality of descriptors. In the described example, extraction of 243 descriptors is performed. These descriptors may be stored and transmitted to remote equipment with high efficiency, because the data occupy very limited space while representing high density information.

The recorded data are transmitted to a remote station connected to the portable device via a switched telephone network, a cellular telephone network or a digital network or even by a dedicated network of the "extranet" type. These data may include one or more recent recordings performed by the patient, optionally, one or more reference recordings, data on the patient's identity and descriptors of the various recordings.

The quality of recognition and reproduction of the artifacts induced by the operation of a pacemaker (spikes) was demonstrated in first experiments which were conducted confidentially.

Figure 3:
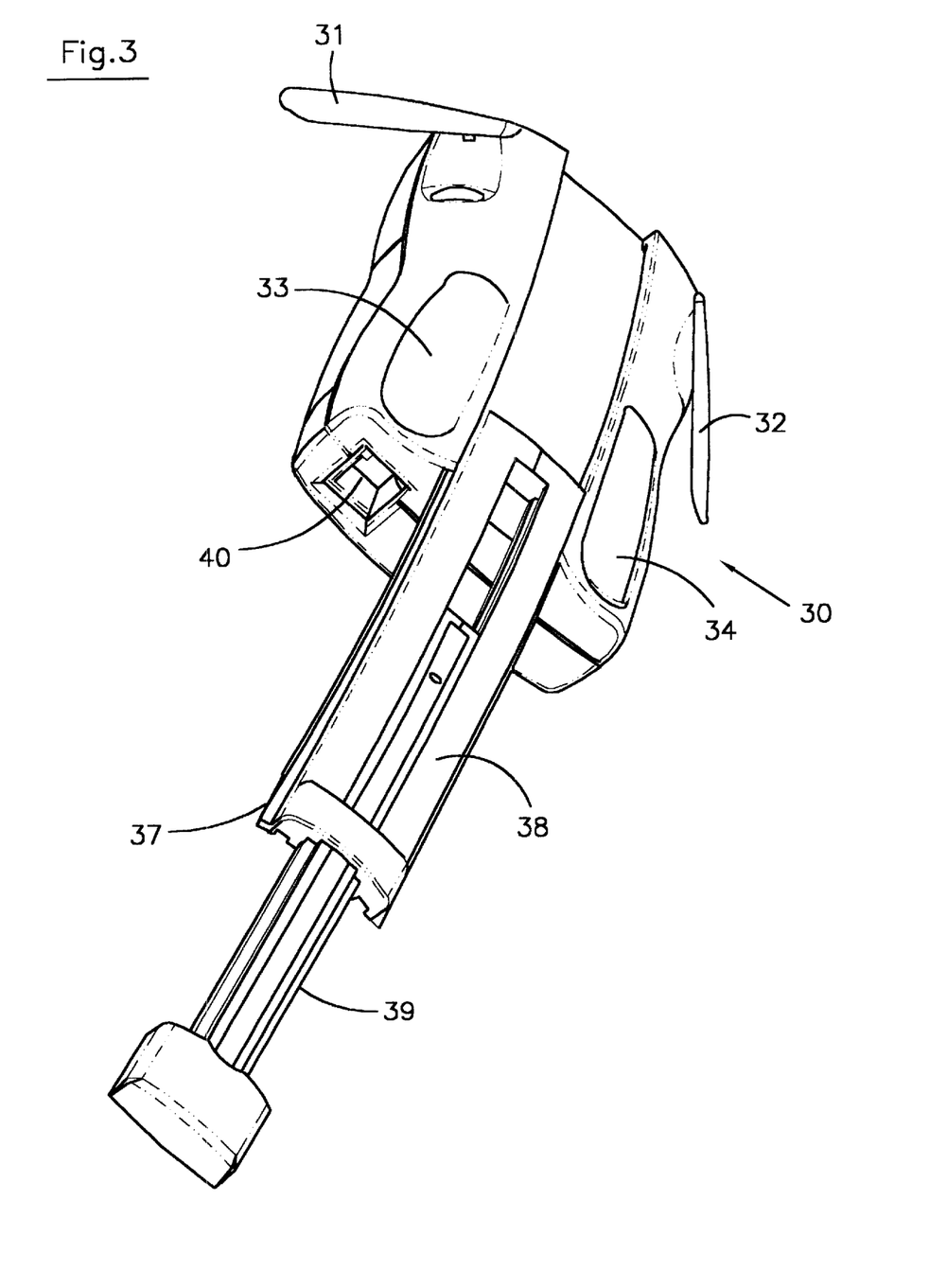
FIGS. 3 and 4 show front and rear perspective views of an alternative embodiment of the device.

FIG. 3 shows an alternative embodiment, wherein a housing 30 has two arms 31, 32. These arms 31, 32 may be retractable for example via a joint enabling them to be folded back against a face or an edge of the housing, to reduce bulk size when the apparatus is not being used. These arms 31, 32 have metal electrodes or electrodes made of plastic filled with metal or made electrically conductive, on their ends. The arms 31, 32 are advantageously inclined in their position of use, with respect to the median axis of the housing, to make positioning of the electrodes easier on the V2 precordial point and on the precordial point located between V4 and V5. The central electrode is held by the housing.

The housing has furthermore two metallized areas 33, 34 for supporting fingers. The housing 30 is provided with a retractable rod which may extend to the groin of the user. This rod is made up of two segments 38, 39 which slide one within the other. The distal segment 39 has an electrode for acquiring a peripheral signal.

The two rods 38, 39 may be made up from strips, jointed by a hinge 37 so that the retractable rod may follow the morphology of the user's body. The distance between the contact under the nipple and the contact of the groin is advantageously between about 240 and 292 centimeters. It may be set to about 250 mm so that it may fit different body shapes. The peripheral electrode may be made in the shape of a bar or a pad. Connection with a telephone set is achieved through connector 40.

Figure 4:
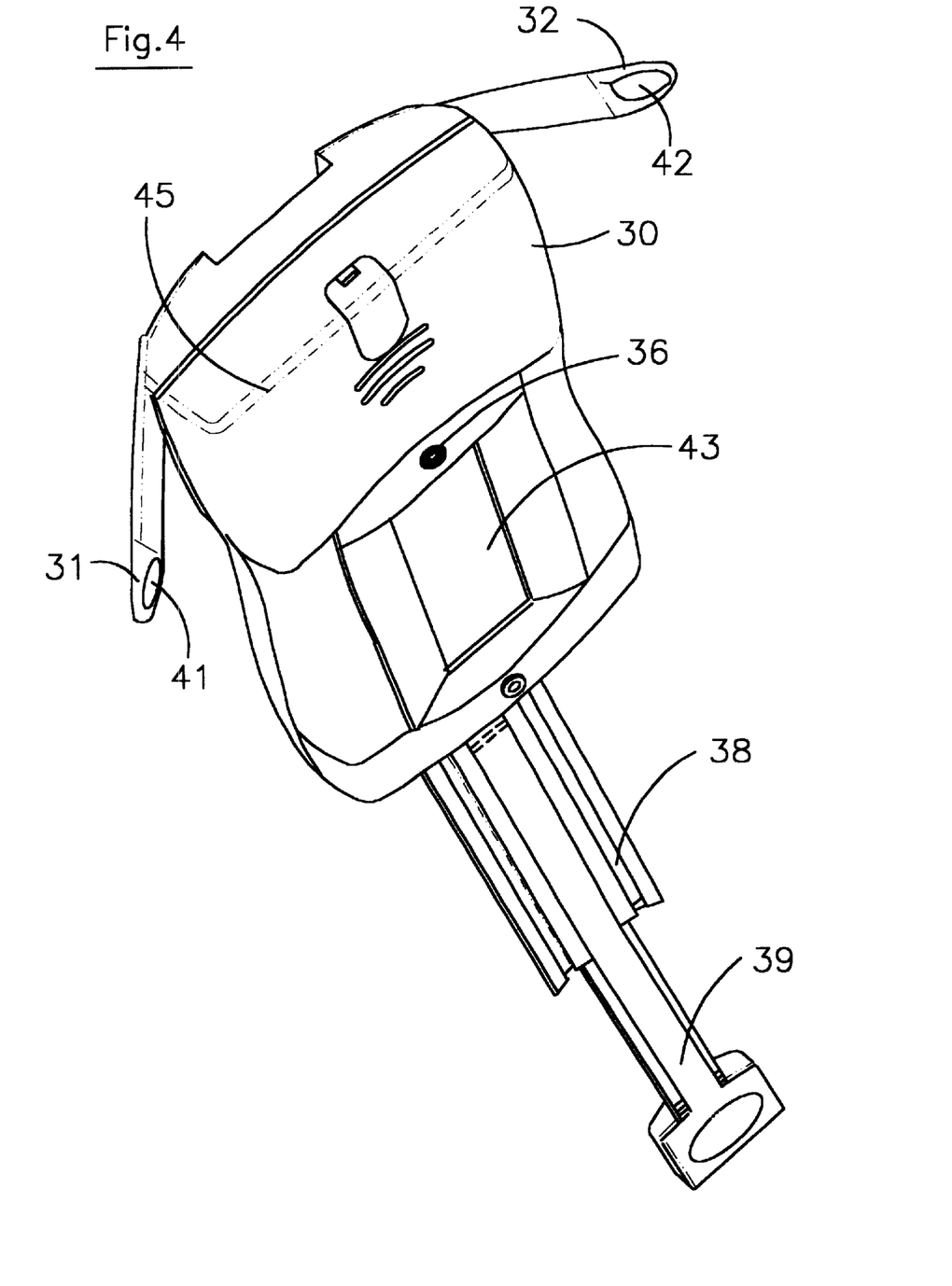

FIG. 4 shows a view of the device from behind. The arms 31, 32 have metallized areas 41, 42 on their ends. The housing has a metallized area 45 for acquiring the neutral signal at the position under the nipple. The strip 39 slides relatively to the strip 38 by following a curved movement, so as to fit to the waist of the user and to body curvatures. A compartment for power batteries is closed by a trapdoor.

Figure 5:
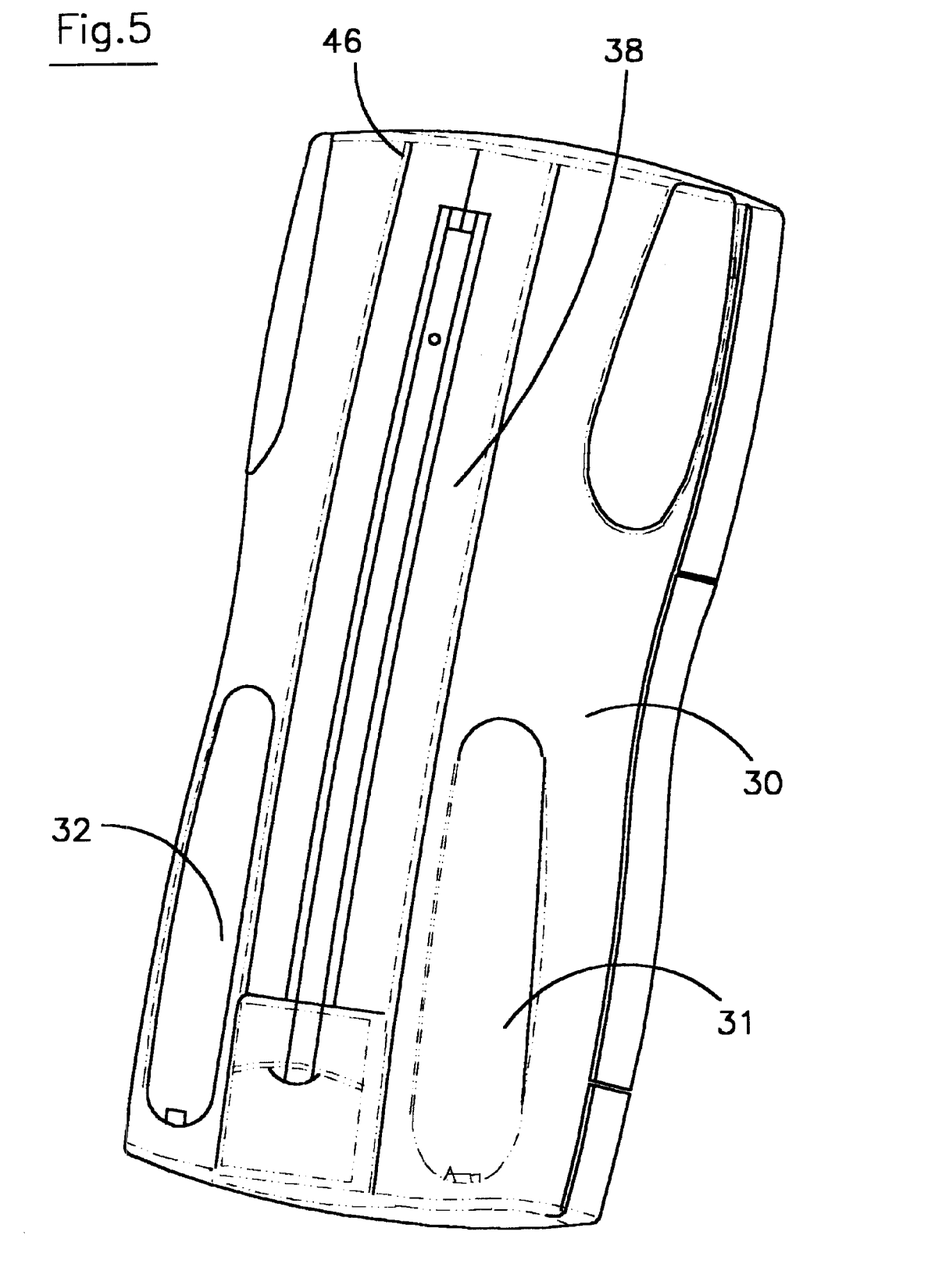
FIG. 5 shows a front perspective view of the embodiment of FIGS. 3 and 4 with the rod retracted and the arms in a folded, transport position.

FIG. 5 represents the device in the transport position. The arms 31, 32 are folded back on the housing 30. The strip 39 is retracted in the strip 38, which itself is pushed back into a compartment provided on the housing 30.

An advantageous protocol for use is described in the following. It includes an initialization phase, prior to using the device.

The initialization phase for the user who has rented, received or purchased the device, consists of performing a first series of one to six acquisitions of electrocardiograms. The ecg signals are stored in the device, in the memory. Next, the user connects the device to the telephone network, for example, through a jack identical to the standard jack of a telephone set. This solution is advantageous because the keyboard of the telephone set may be used in the usual way, and the handset of the telephone set may simply be replaced with the ecg acquisition device. The latter may comprise a microphone and a loudspeaker in order to allow interaction with an operator.

Switching from a vocal mode to a data transmission mode is done manually, by the user actuating a key for triggering the data transmission procedure. This may also be triggered remotely, by the server or by an operator. The ecg parameter series is transmitted to the processing center which makes use of these data in order to determine which of these percritical plots may be selected as reference plot.

After this selection, the processing center proceeds with initialization of the device by transmitting information such as an identifier of the patient, data pertaining to the patient and/or to his attending physician, or even a part of his medical file, and with deletion of the plots other than the selected plot in order to form the reference plot.

On board memory in the housing may include:
The identification of the patient
The subscription status
The reference plot.

In the event of a seizure, the patient transmits these data after a local discussion, as well as the plot which he has just recorded. Optionally, communications with the processing center may be established through an integrated GSM module in the housing.

The solution provided by the invention comprises selecting a reduced number of precordial signals and proceeding with acquisition of the upper peripheral signals through electrodes positioned on the housing, on which the thumb may be applied.

By reducing the number of precordial electrodes to three, proper application of the electrodes on the thorax is performed under good conditions. Actually, it is easy to apply three points on the curved surface of the thorax, whatever the patient's morphology. Moreover, the transmission suggested in the WO94/03106 document, as DTMF signals, is too slow and does not allow the signals to be exploited satisfactorily.

Thus, the invention avoids the drawbacks of the prior art by providing a device for recording an electrocardiogram which may be effectively and ergonomically used by the patient himself, or by staff having a low level of qualification. In particular, the invention simplifies signal acquisition and making signal quality more independent of skin electrode positioning and fixing problems. Another important aspect of the invention allows information to be acquired for analyzing repolarization abnormalities and not only those of arrhythmia. These abnormalities allow a physician having the recording of the signals at his disposal, to diagnostic pathologies such as coronary spasms, angina cordis, infraction, mitral insufficiencies, cardiovascular accidents and also to localize the abnormality. Consequently, such a device is particularly adapted to the needs of wearers of pacemakers.

For this purpose, this invention concerns, in its broad sense, a device comprising a portable housing and means for acquiring, processing and storing electrical signals delivered by electrodes, characterized in that the housing has on one face, a first series of three metal electrodes positioned so that they may be applied on the patient's thorax for acquiring three precordial signals and a second series of two metal electrodes positioned on the other face so that the thumbs can be applied for acquiring two peripheral signals, as well as a skin electrode for acquiring a third peripheral signal, connected to the housing by a connecting cable.

One important characteristic of the invention relates to the choice of the precordial and peripheral acquired signals. It has appeared that by choosing to acquire only three precordial signals, the quality of the recording of an electrocardiogram by the patient may be considerably improved. Actually, the quality of the ecg recording largely depends on the conditions of application of the electrodes on the patient's body. If they are badly applied, or if there is a change in the applied pressure, the acquired bio-electrical signals are strongly disrupted and cannot be utilized satisfactorily. None of the prior art devices comes up with a satisfactory solution to the problem posed by the acquisition of a complete and good quality ecg signal by a moderately experienced user.

The device may thus directly acquire five leads, and calculate three additional leads, by simply applying the housing against the thorax, and by only placing one skin electrode.

As previously described above, the position of the first series of electrodes is preferably determined so that the central electrode may be applied at the patient's left nipple, corresponding to the V3 precordial point, and the side electrodes may be applied on both sides of the patient's nipple, corresponding to the V2 precordial point and to a point located between the V4 and V5 precordial points, respectively.

According to a preferred embodiment, the first series of electrodes is positioned on the concave side face of the housing and in such a way that the second series of electrodes is positioned on both sides of the upper face of the housing, whereby the housing's shape is determined so as to allow it to be held with two hands, between the thumbs pressing against the two electrodes of the second series respectively and the forefingers.

Advantageously, the device includes a graphic display for displaying a previously acquired and stored plot, for displaying all the plots, especially the percritical electrocardiogram's plot, and/or for displaying information pertaining to the patient. This embodiment has an essential technical effect: a physician is able to proceed immediately with an analysis of the electrocardiogram recorded by the patient. The alleged seizure situation may relatively often arise in a public place, for example, a shop, an aircraft, a train. In such a situation, the patient may proceed with recording his electrocardiogram and show the device to a physician present in the public place so that he may view the electrocardiogram and proceed with analysis on the spot. This alternative is also adapted to medicine in the field, in medically badly equipped areas. Medical staff equipped with light and portable means may then proceed with examinations which up to now were reserved to practices equipped with costly hardware. Preferably, the device includes a modem for transmitting recorded information to remote equipment.

According to an other alternative, the device includes a connector for a peripheral, for example a micro-computer or a printer, whereby said connector is protected by a trapdoor which may be closed by a flap which actuates in the open position a contactor ensuring disconnection of the electrodes. This embodiment prevents risks of electrocution, even if the user attempts to proceed with a wrong connection.

Advantageously, the device includes means for storing at least a procedure for accessing remote equipment. This procedure may simply consist of the telephone number, or of a more elaborate procedure comprising steps for detecting reception by the remote equipment and for transmitting to other equipment if the former is not enabled.

According to another advantageous alternative, the device includes means for storing at least a piece of information for identifying the user of the device, wherein said information may be transmitted by modem and displayed on the device's display.

According to another alternative, the device includes a socket for connecting a universal connector having means for connection, compatible with a plurality of electrocardiographs. This alternative provides connection to any standard electrocardiograph, a pen electrocardiograph for example, for making use of the information recorded by the patient under a format which the physician is used to.

Preferentially, the device includes means for storing at least a reference electrocardiogram and a plurality of electrocardiograms recorded in a re-recordable buffer memory. According to a particular application, two reference electrocardiograms are recorded, one with the enabled pacemaker, the other with the disabled pacemaker.

According to a preferred alternative, the device includes means for calculating a plurality of descriptors corresponding to the signals acquired through these electrodes, wherein said descriptors are stored and suitable for being transmitted to the remote equipment. The invention further relates to equipment for interpreting electrocardiograms recorded by a portable device, wherein a micro-computer is provided with its own means for receiving, storing and displaying information transmitted by said portable device.

We claim:

1. Apparatus for recording an electrocardiogram comprising:
    a portable housing; and
    an analyzer which acquires, processes and stores electrical signals delivered by electrodes positioned on said housing such that said electrodes are capable of being applied to a patient's thorax, and
    wherein said housing has i) a three metallic precordial electrodes positioned for application on said patient's thorax to acquire three precordial signals, ii) two metallic peripheral electrodes positioned on said housing and adapted so that a patient's fingers on both hands are capable of being applied to the electrodes to acquire two peripheral signals, iii) a skin electrode to acquire a third peripheral signal, and iv) a cable connected between said housing and said skin electrode.

2. The apparatus according to claim 1, wherein the position of said precordial electrodes is dimensioned so that the central electrode is capable of being applied at or adjacent the left nipple of the patient, corresponding to a V3 precordial point on the patient, and the other electrodes of said precordial electrodes are capable of being applied at or on both sides of the nipple, corresponding to a V2 precordial point on the patient and to a point located between V4 and V5 precordial points on the patient, respectively.

3. The apparatus according to claim 2, wherein the housing has a concave side and an upper face, and the first series of electrodes is positioned on a face of the concave side of the housing, and wherein the second series of electrodes is positioned on both sides of the upper face of the housing, wherein the shape of the housing is dimensioned so that it is capable of being held with both hands, between thumbs pressing on the two electrodes of the second series and forefingers, respectively.

4. The apparatus according to claim 1, wherein the analyzer acquires and records a plot and further comprises a graphic display for displaying a previously acquired and stored plot.

5. The apparatus according to claim 1 further comprising remote equipment and means for storing at least a procedure for accessing the remote equipment.

6. The apparatus according to claim 1 further comprising a modem, a display and means associated with the housing for storing at least a piece of information for identifying the user of the device, wherein said information is capable of being transmitted by the modem and displayed on the display.

7. The apparatus according to claim 6 further comprising a pacemaker, first means for recording a reference electrocardiogram associated with the pacemaker and second means for recording associated with the pacemaker, wherein the pacemaker is capable of being enabled or disabled.

8. The apparatus according to claim 1 further comprising a socket in the housing for connecting a universal connector having connection means capable of being connected to a plurality of electrocardiographs.

9. The apparatus according to claim 1 further comprising a recordable buffer memory associated with the housing and means for storing at least a reference electrocardiogram and a plurality of recorded electrocardiograms in the re-recordable buffer memory.

10. Apparatus for recording an electrocardiogram comprising:
    a portable housing; and
    an analyzer which acquires, processes and stores electrical signals delivered by electrodes positioned on said housing such that said electrodes are capable of being applied to a patient's thorax, and
    wherein said housing has i) three metallic precordial electrodes positioned for application on said patient's thorax to acquire three precordial signals, ii) two metallic peripheral electrodes positioned on said housing and adapted so that a patient's fingers are capable of being applied to the electrodes to acquire two peripheral signals, iii) a skin electrode to acquire a third peripheral signal, and iv) a cable connected between said housing and said skin electrode, and a connector for connecting a peripheral device for recording an electrocardiogram, said connector comprising a trapdoor, a flap, a contactor, and a socket protected by said trapdoor which is capable of being closed by said flap which in the open position actuates said contactor ensuring disconnection of the electrodes.

11. Apparatus for recording an electrocardiogram comprising:
    a portable housing; and
    an analyzer which acquires, processes and stores electrical signals delivered by electrodes positioned on said housing such that said electrodes are capable of being applied to a patient's thorax, and
    wherein said housing has i) three metallic precordial electrodes positioned for application on said patient's thorax to acquire three precordial signals, ii) two metallic peripheral electrodes positioned on said housing and adapted so that a patient's fingers are capable of being applied to the electrodes to acquire two peripheral signals, iii) a skin electrode to acquire a third peripheral signal, iv) two side arms each bearing one of said precordial electrodes and a retractable rod including said third peripheral electrode at an end thereof.

12. The apparatus according to claim 11 wherein the arms are inclined with respect to a median axis of the housing.

13. The apparatus according to claim 11, wherein the arms are jointed for swinging between an extended position and a folded back position against the side faces of the housing.

14. The apparatus according to claim 11, further comprising a hinge and a set of two retractable strips jointed by the hinge, wherein the peripheral electrode is fixed to an end portion of the set of two retractable strips.

15. Apparatus for recording an electrocardiogram comprising:
    a portable housing; and
    an analyzer which acquires, processes and stores electrical signals delivered by electrodes positioned on said housing such that said electrodes are capable of being applied to a patient's thorax, and
    wherein said housing has i) three metallic precordial electrodes positioned for application on said patient's thorax to acquire three precordial signals, ii) two metallic peripheral electrodes positioned on said areas of said housing and adapted so that a patient's thumbs are capable of being applied to said electrodes to acquire two peripheral signals, iii) a skin electrode to acquire a third peripheral signal, and iv) a cable connected between said housing and said skin electrode.

16. A system for interpreting electrocardiograms from a patient recorded by a portable device capable of transmitting signals comprising:
- a device for recording an electrocardiogram including a portable housing and an analyzer which acquires, processes and stores electrical signals delivered by electrodes,
- wherein said housing has i) three metal precordial electrodes positioned so that they are capable of being applied on said patient's thorax to acquire three precordial signals ii) two metal peripheral electrodes positioned so that the patient's thumbs on both hands are capable of being applied to the electrodes for acquiring two peripheral signals, iii) a skin electrode for acquiring a third peripheral signal, iv) a cable connected between said housing and said skin electrode and, v) a microcomputer capable of receiving, storing and displaying the signals transmitted by said portable device.

* * * * *